(12) United States Patent
Domen et al.

(10) Patent No.: US 7,335,790 B2
(45) Date of Patent: Feb. 26, 2008

(54) POLYCYCLIC AROMATIC CARBON BASED SOLID STRONG ACID

(75) Inventors: Kazunari Domen, Kanagawa (JP); Michikazu Hara, Kanagawa (JP)

(73) Assignee: Japan Science and Technology Agency, Saitama (JP)

( * ) Notice: Subject to any disclaimer, the term of this patent is extended or adjusted under 35 U.S.C. 154(b) by 175 days.

(21) Appl. No.: 10/544,402

(22) PCT Filed: Sep. 8, 2003

(86) PCT No.: PCT/JP03/11442

§ 371 (c)(1),
(2), (4) Date: Aug. 3, 2005

(87) PCT Pub. No.: WO2004/069789

PCT Pub. Date: Aug. 19, 2004

(65) Prior Publication Data

US 2006/0276668 A1    Dec. 7, 2006

(30) Foreign Application Priority Data

Feb. 5, 2003    (JP)    ............... 2003-027810

(51) Int. Cl.
*C07C 309/38*    (2006.01)
(52) U.S. Cl. ................................. 562/89
(58) Field of Classification Search .......... 562/32
See application file for complete search history.

(56) References Cited

U.S. PATENT DOCUMENTS 2,585,983 A * 2/1952 Adams et al. .............. 585/451

FOREIGN PATENT DOCUMENTS

| EP | 0 383 995 | 8/1990 |
|----|-----------|--------|
| EP | 1 667 167 | 6/2006 |
| JP | 63-097624 | 4/1988 |
| WO | WO 98/30519 | 7/1998 |

OTHER PUBLICATIONS

Ishihara, et al., Polystyrene-Bound Tetrafluorophenylbis(triflyl)methane as an Organic-Solvent-Swellable and Strong Bronsted Acid Catalyst, Angew. Chem. Int. Ed. 2001, 40, No. 21, pp. 4077-4079.

* cited by examiner

*Primary Examiner*—Yvonne Eyler
*Assistant Examiner*—Valenrod Yevgeny
(74) *Attorney, Agent, or Firm*—Hahn & Voight PLLC; Roger C. Hahn (57) ABSTRACT

A composite solid strong acid comprising, a solid acid and a carbon material, wherein said solid acid is obtained by heat treating of polycyclic aromatic hydrocarbons or polycyclic aromatic hydrocarbons to which the carbon material is blended in concentrated sulfuric acid or fuming sulfuric acid, transforming said polycyclic aromatic hydrocarbons to a solid acid which is insoluble in a polar solvent by condensation and sulfonation further compositing with said carbon material.

17 Claims, 10 Drawing Sheets

POLYCYCLIC AROMATIC CARBON BASED SOLID STRONG ACID

FIELD OF THE INVENTION

The present invention relates to a solid acid insoluble in a polar solvent obtained by a process characterizing that polycyclic aromatic hydrocarbon or polycyclic aromatic hydrocarbon to which carbon material is blended is heat-treated in conc. sulfuric acid or in fuming sulfuric acid, then the polycyclic aromatic hydrocarbon is condensed and sulfonated, or composed with carbon materials which is blended at the condensation or sulfonation reaction, or a composite solid strong acid composed by said solid acid and carbon material and an use of said solid acid as a solid strong acid catalyst.

DESCRIPTION OF THE PRIOR ART

Currently, energy situations or environmental situations are in critical situation, and it is required to produce only a subjected product alone effectively by small energy without producing unnecessary by-product. Acid catalyst is necessary for chemical industries of the present age, and used in production of various products such as chemicals, products of petrochemical industry or polymer products, and considerable parts of the acid catalysts are a liquid acid such as hydrochloric acid or sulfuric acid. The liquid acid catalyst used in a production process is separated from the product and recovered by means of processes of neutralization with a base and removal of salt which is formed by the neutralization. However, energy consumed for the neutralization process and the removal process of salt occupies considerable parts in total energy used in all production processes. And the recovered salts are over supply in a market, further, since mostly of these salts are by-products whose utilizability is small, in many cases, treatment of these salts are difficult.

In such a circumstance, a solid acid does not need said neutralization process or removing process of salt for separation and recovery, does not form unnecessary by-products and can produce an objected product by lower energy. Therefore, investigation was carried out in early stage (Ishihara, K; Hasegawa, A; Yamamoto, H. Angew. Chem. Int. Ed. 2001, 40, 4077; Document 1). As the results of the investigation, a solid acid catalyst such as zeolite, silica alumina or hydrous niobate obtains good results in chemical industries and provides good benefit to human society. Further, as a strong acid polymer, material prepared by sulfonation of polystyrene can be considered as a solid acid and has been used as a cationic ion-exchange resin which indicates acidity for a long time. Furthermore, Nafion (T.M. of Du-pont) which loads sulfone group on polytetrafuluoroethylene skeleton is known as a very strong solid acid (solid super strong acid) having hydrophilicity, and it is well known that these acid polymers act as a super strong acid having acid strength stronger than liquid acid. However, polymer has problems that it is weak to heat and is too expensive for an industrial use. Accordingly, from the view points of performance and cost, it is very difficult to design more advantageous industrial process by using solid acid catalyst than industrial process using liquid acid catalyst, therefore, almost all chemical industries depend on liquid acid catalyst. Considering said circumstance, development of a solid acid catalyst that exceeds a liquid acid catalyst from view points of performance and cost has been desired.

Further, as an inorganic type, although sulfuric acid trace zirconia prepared by sulfuric acid treatment of zirconium oxide ($ZrO_2$) is a solid acid catalyst having the strongest acidity, the amount of sulfuric acid trace is not so large, and numbers of acid point per unit weight is smaller than that of liquid acid, therefore, it is hard to satisfy said requirement.

The subject of the present invention is to provide a solid acid catalyst which dissolves said problems and can be advantageously usable for an industrial use. The inventors of the present invention think about a structure characterizing that sulfuric groups are loaded to a chemical material possessing a basic backbone which is stable against physical action such as heat, and pay attention to use a polycyclic hydrocarbon compounds characterizing that many aromatic compound rings, which are contained in tar, pitch, fuel oil or asphalt, are condensed as a composing material of said basic backbone. The inventors of the present invention use tar, pitch, fuel oil or asphalt itself or a polycyclic hydrocarbon compounds characterizing that many aromatic compound rings are condensed as a composing material of said basic backbone, heat treated them in concentrated sulfuric acid or fuming sulfuric acid, and the chemical structural feature and acid characteristic of the obtained product are investigated, and found out that condensation reaction of the composing material of said basic backbone is progressed simultaneously with sulfonation and an useful material as a solid acid which can be used stable in high temperature condition can be obtained. Further, the inventors of the present invention carried out esterfication reaction of ethylalcohol and acetic acid by trial, and find out that said reaction is remarkably accelerated by presence of said solid acid and is useful as a solid acid catalyst, thus the subject can be accomplished. Further, in an investigation to obtain a solid acid material which improves the characteristics of said obtained solid acid, carbon materials such as activated carbon or acetylene black are blended to the material of said solid acid and heat treated in concentrated sulfuric acid or fuming sulfuric acid, and find out that a composite solid acid of polycyclic aromatic carbon solid acid—carbon material can be obtained.

SUMMARY OF THE INVENTION

The first one of the present invention is (1) a solid acid, which is insoluble in a polar solvent, obtained by heat treating of polycyclic aromatic hydrocarbons in concentrated sulfuric acid or fuming sulfuric acid to thereby condense and sulfonate said polycyclic aromatic hydrocarbons. Desirably, the first one of the present invention is (2) the solid acid of (1) wherein, the polycyclic aromatic hydrocarbons is at least one selected from the group consisting of a polycyclic aromatic hydrocarbon obtained by condensing two or more aromatic rings, mixture of a polycyclic aromatic hydrocarbon obtained by condensing two or more aromatic rings or tar, pitch, fuel oil or asphalt containing a polycyclic aromatic hydrocarbon obtained by condensing two or more aromatic rings, more desirably, the first one of the present invention is (3) the solid acid of (1) or (2) wherein, temperature T for heat treatment is $100°\,C. \leq T \leq 450°\,C.$, further desirably the first one of the present invention is (4) the solid acid of (3) wherein, the temperature T for heat treatment is $200°\,C. \leq T \leq 350°\,C.$ The second one of the present invention is (5) a solid strong acid catalyst comprising the solid acid of (1) which is insoluble in a polar solvent. Desirably, the second one of the present invention is (6) the solid strong acid catalyst comprising the solid acid of (2) which is insoluble in a polar solvent, more desirably, the second one of the present invention is (7) the solid strong acid catalyst comprising the solid acid of (2) which is insoluble in a polar solvent, further desirably the second one of the present invention is (8) the solid strong acid catalyst comprising the solid acid of (4) which is insoluble in a polar solvent.

The third one of the present invention is (9) a composite solid strong acid comprising a solid acid and a carbon material, wherein said solid acid is obtained by heat treating of polycyclic aromatic hydrocarbons to which the carbon material is blended in concentrated sulfuric acid or fuming sulfuric acid, transforming said polycyclic aromatic hydrocarbons to a solid acid which is insoluble in a polar solvent by condensation and sulfonation further compositing with said carbon material. Desirably, the third one of the present invention is (10) the composite solid strong acid of (9), wherein the aromatic hydrocarbons is at least one selected from the group consisting of a polycyclic aromatic hydrocarbon obtained by condensing two or more aromatic rings, mixture of a polycyclic aromatic hydrocarbon obtained by condensing two or more aromatic rings or tar, pitch, fuel oil or asphalt containing a polycyclic aromatic hydrocarbon obtained by condensing two or more aromatic rings, more desirably, the third one of the present invention is (11) the composite solid strong acid of (9) or (10), wherein temperature T for heat treatment is $100°C. \leq T \leq 450°C.$, further desirably the third one of the present invention is (12) the solid acid of (11) wherein, the temperature T for heat treatment is $200°C. \leq T \leq 350°C.$, furthermore desirably, the third one of the present invention is (13) the composite solid strong acid of (9), (10), (11) or (12), wherein, the carbon material is at least one selected from the group consisting of carbon black, acetylene black, activated carbon, carbon nano tube or fullerene.

DESCRIPTION OF THE PREFERRED EMBODIMENT

The present invention will be illustrated more in detail.

I. The acid catalyst of the present invention, which is insoluble in a polar solvent, can be obtained by heat treating of polycyclic aromatic hydrocarbons contained in pitch, tar, fuel oil or asphalt in concentrated sulfuric acid or fuming sulfuric acid, and condensation reaction of said polycyclic aromatic hydrocarbons is progressed simultaneously with sulfonation reaction, therefore stabilized chemical structure is formed. Further, said solid acid indicates strong acidity and is useful as a solid strong acid catalyst and has a advantageous that it can be synthesized by lower cost.

As an example of a polar solvent in which said solid acid is insoluble, water, alcohol, aldehyde, carboxylic acid, ketone, amine or imine can be mentioned.

II. As a polycyclic aromatic hydrocarbons, compound characterized at least two aromatic rings are condensed can be use as a starting material for synthesis of a solid acid of the present invention, however, when degree of condensation is too small, time for synthesis of solid acid becomes long, therefore, it is desirable to use a compound characterized at least five aromatic rings are condensed as a starting material to obtain stable solid acid from the view point of industrial production.

It is well known that the polycyclic aromatic hydrocarbons are polycondensed in concentrated sulfuric acid or fuming sulfuric acid and an amorphous material characterized that polycyclic aromatic hydrocarbons are complexly polycondensed is formed, further, the property of it becomes closer to that of graphite along with the increase of the numbers of aromatic rings.

The inventors of the present invention, predicts that polycyclic aromatic hydrocarbon characterized that many aromatic rings are condensed forms the structure which progressed to two dimensional shape similar to graphite, and even if the outermost aromatic rings are sulfonated, it becomes a solid acid which is insoluble in water based on the largely advanced structure of hydrophobic polycyclic aromatic hydrocarbon, and tried heat treatment indicated by following formula 1. Formula 1 indicates a concept of the present invention in a case that plural aromatic hydrocarbons are used as a starting material.

Formula 1

Said polycyclic aromatic hydrocarbon composed of naphthalene, anthracene, perylene or coronene is heat treated in concentrated sulfuric acid or fuming sulfuric acid and sulfonation and polycondensation reactions are carried out. By said sulfonation and polycondensation reactions, amorphous carbon material characterized that many sulfonated polycyclic aromatic hydrocarbons are condensed can be obtained.

When treating temperature in concentrated sulfuric acid or fuming sulfuric acid is lower than 100° C., since polycondensation of the polycyclic aromatic hydrocarbon does not progress sufficiently and a polycyclic aromatic hydrocarbon composed of many aromatic rings is not formed, a solid acid which is insoluble in a polar solvent can not be obtained. On the contrary, when the treating temperature exceeds 450° C., insoluble amorphous hydro carbon in which sufficient amount of sulfone group to occur heat decomposition of sulfone group is existing.

More desirable heat treatment temperature is 200-350° C. The solid acid catalyst of the present invention can be synthesized not only by starting material composed of single polycyclic aromatic hydrocarbon but also by starting material composed of plural polycyclic aromatic hydrocarbons. Further, the solid acid catalyst of the present invention can be synthesized using pitch, tar, fuel oil or asphalt in which various polycyclic aromatic hydrocarbons, saturated hydrocarbon or unsaturated hydrocarbon are contained or mixture thereof as starting materials for synthesis.

III. As a carbon material used for the synthesis for a composite solid strong acid by blending with starting materials for synthesis of said polycyclic aromatic hydrocarbons, carbon black, acetylene black, activated carbon (granular state, whisker state, pulp state), graphite, carbon nano tube or fullerene, which are characterized to hold formed solid acid as a carrier for solid catalyst, desirably, a carbon material having surface structure to the surface of which many sulfate roots can be arranged, can be mentioned.

EXAMPLE

The present invention will be illustrated more specifically according to the Examples, however, not intending to limit the scope of the present invention.

Measuring Apparatus;
A. Crystalline characteristic of synthesized solid acid catalyst is measured by an X-ray diffraction instrument, Geigerglex RAD-B, Cu Kα, product of Rigaku Co., Ltd.
B. Elementary analysis, sulfur content is measured using CHNS-932, product of LECO Co., Ltd., by burning a specimen under oxygen gas flow.
C. Stability of sulfone group is measured by temperature-programmed desorption (Multi Task TPD, product of Japan Bell Co., Ltd.) and thermogravimetric analysis (DTG-60/60H, product of Shimazu Co., Ltd.).

Example 1

Figure 1:
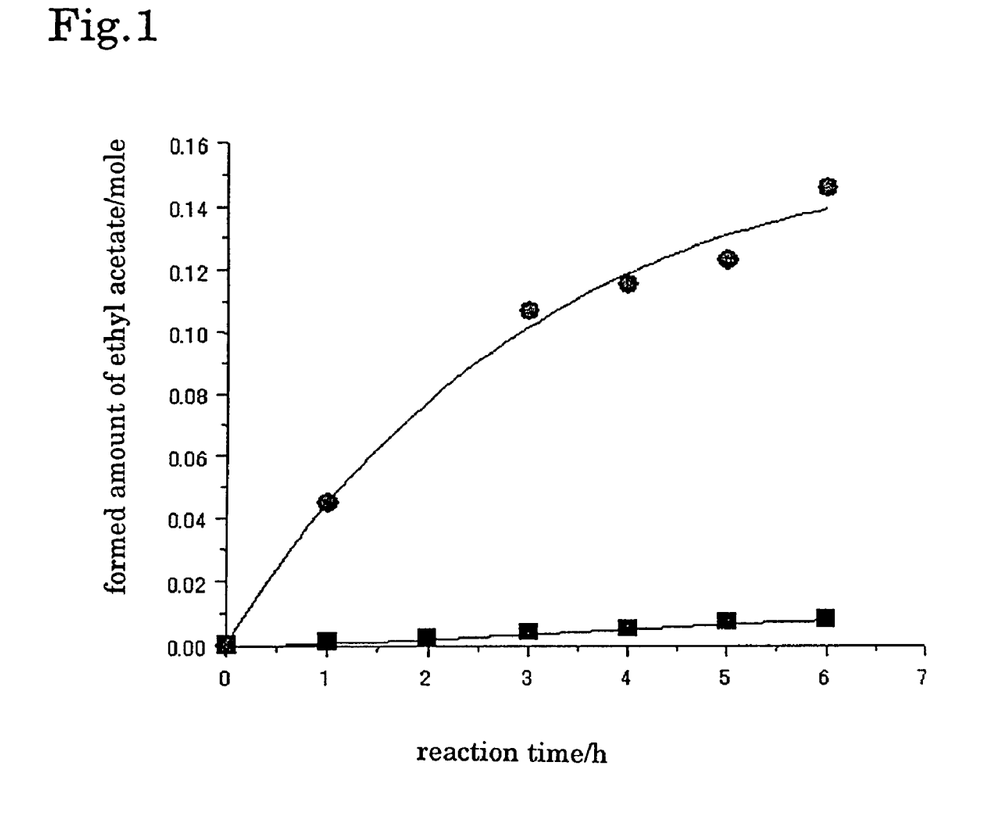
FIG. 1 shows catalytic activity of a solid acid obtained in Example 1 when it is used as an acid catalyst for esterfication reaction of ethanol and acetic acid (● catalyst is existing, ■ without catalyst. These marks are same in FIGS. 2-5).

1.00 g of coronene ($C_{24}H_{12}$) is added to 100 mL of conc. sulfuric acid (96%) and heated at 200° C. for 8 hours. Excess conc. sulfuric acid is removed by vacuum distillation at 250° C., then black solid powder is obtained. This solid powder is washed by 300 mL of ethyl alcohol, and the washing process is repeated until sulfuric acid contained in ethyl alcohol after washed becomes under detection limit of elementary analysis. Since from X-ray diffraction pattern of the obtained black powder, any structure is not observed, this material is understood to be amorphous. From elementary analysis, sulfur content of this polycyclic aromatic carbon solid strong acid is 1.5 atm %, and presence of many sulfonic acid groups are detected. From the results of temperature-programmed desorption and thermogravimetric analysis, it is confirmed that the decomposition temperature of the polycyclic aromatic carbon solid strong acid in atmosphere is 210° C., and is understood that thermo stability of it is high. Above mentioned black powder is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 1. In FIG. 1, for the comparison, formation of ethyl acetate by reaction without catalyst is also shown by time lapse. As shown in FIG. 1, forming speed of ethyl acetate in the presence of synthesized catalyst is remarkably high, and it is understood that the synthesized material acts as a strong solid acid catalyst.

Example 2

Figure 2:
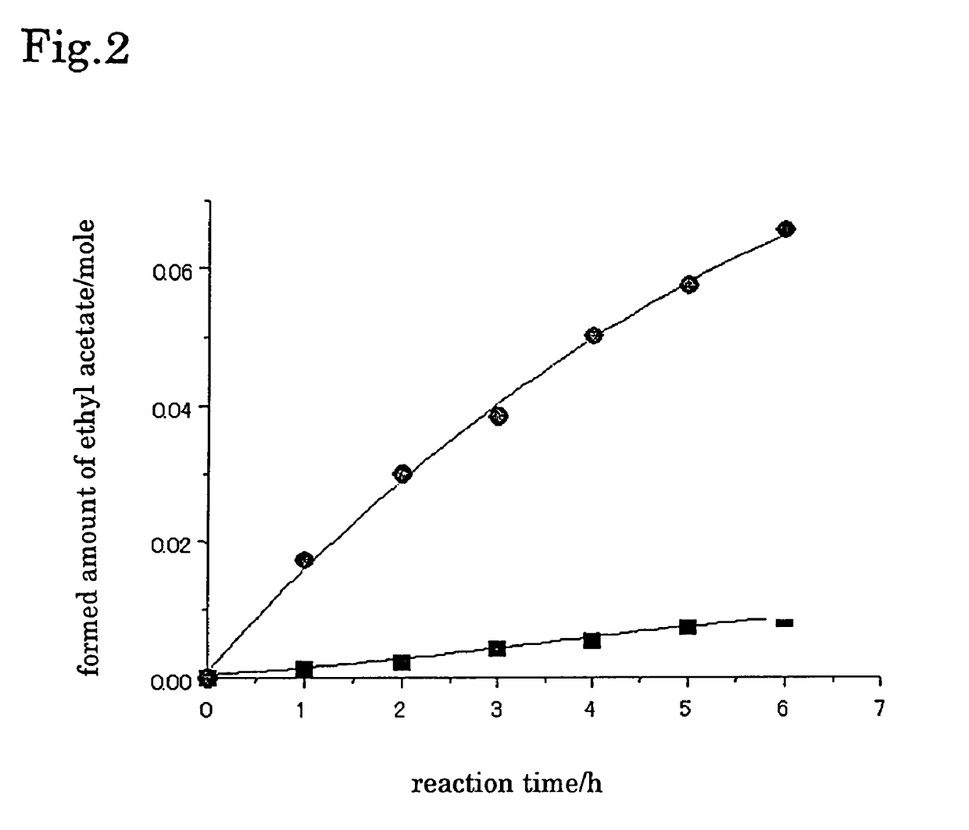
FIG. 2 shows catalytic activity of a solid acid obtained in Example 2 when it is used as an acid catalyst for esterfication reaction of ethanol and acetic acid.

1.00 g of coronene ($C_{24}H_{12}$) is added to 100 mL of conc. sulfuric acid (96%) and heated at 300° C. for 8 hours. Excess conc. sulfuric acid is removed by vacuum distillation at 300° C., then black solid powder is obtained. This solid powder is washed by 300 mL of ethyl alcohol, and the washing process is repeated until sulfuric acid contained in ethyl alcohol after washed becomes under detection limit of elementary analysis. Since from X-ray diffraction pattern of the obtained black powder, any structure is not observed, this material is understood to be amorphous. From elementary analysis, sulfur content of this polycyclic aromatic carbon solid strong acid is 0.8 atm %, and presence of many sulfonic acid groups are detected. From the results of temperature-programmed desorption and thermogravimetric analysis, it is confirmed that the decomposition temperature of the polycyclic aromatic carbon solid strong acid in atmosphere is 230° C., and is understood that thermo stability of it is high. Above mentioned black powder is evacuated at 150° C. for 1 hour, then 0.2 g of it is added as a catalyst into mixed solution of 1.0 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 2. In FIG. 2, for the comparison, formation of ethyl acetate by reaction without catalyst is also shown by time lapse. As shown in FIG. 2, forming speed of ethyl acetate in the presence of synthesized catalyst is remarkably high, and it is understood that the synthesized material acts as a strong solid acid catalyst.

Example 3

Figure 3:
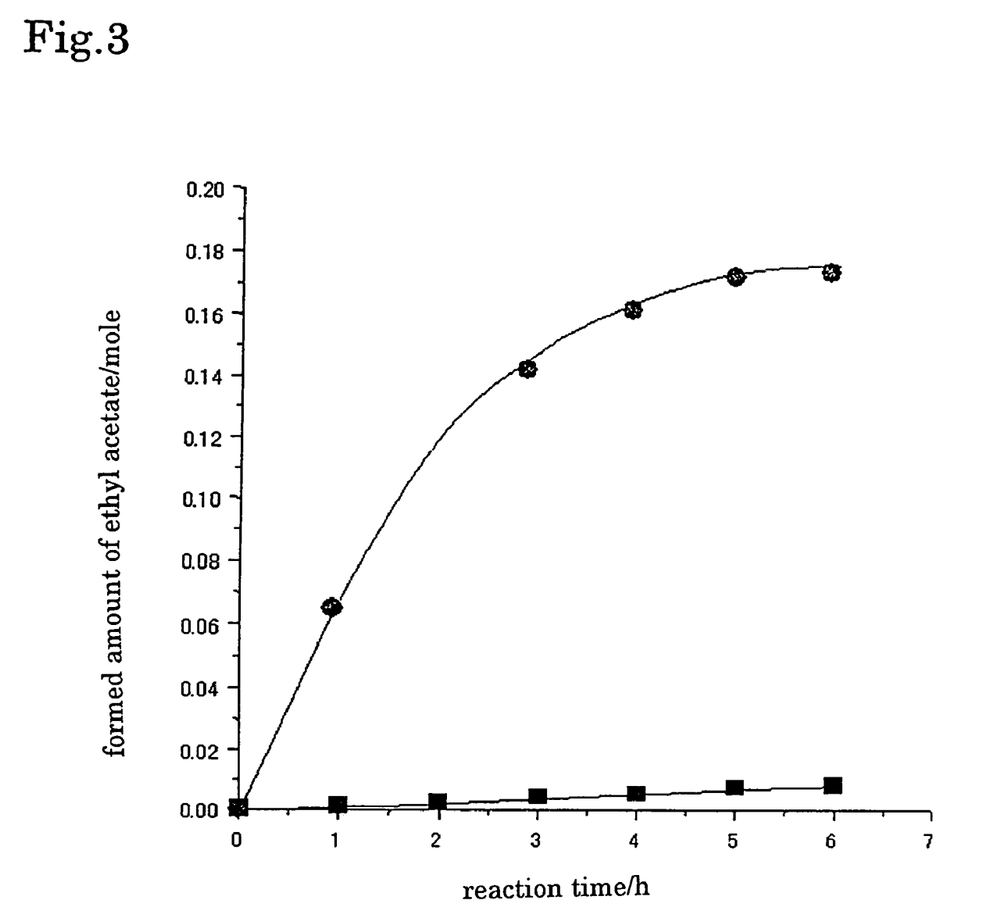
FIG. 3 shows catalytic activity of a solid acid obtained in Example 3 when it is used as an acid catalyst for esterfication reaction of ethanol and acetic acid.

0.50 g of coronene ($C_{24}H_{12}$) and 0.20 g of anthracene are added to 100 mL of conc. sulfuric acid (96%) and heated at 300° C. for 8 hours. Excess conc. sulfuric acid is removed by vacuum distillation at 300° C., then black solid powder is obtained. This solid powder is washed by 300 mL of ethyl alcohol, and the washing process is repeated until sulfuric acid contained in ethyl alcohol after washed becomes under detection limit of elementary analysis. Since from X-ray diffraction pattern of the obtained black powder, any structure is not observed, this material is understood to be amorphous. From elementary analysis, sulfur content of this polycyclic aromatic carbon solid strong acid is 4.5 atm %, and presence of many sulfonic acid groups are detected. From the results of temperature-programmed desorption and thermogravimetric analysis, it is confirmed that the decomposition temperature of the polycyclic aromatic carbon solid strong acid in atmosphere is 210° C., and is understood that thermo stability of it is high. Above mentioned black powder is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 3. In FIG. 3, for the comparison, formation of ethyl acetate by reaction without catalyst is also shown by time lapse. As shown in FIG. 3, forming speed of ethyl acetate in the presence of synthesized catalyst is remarkably high, and it is understood that the synthesized material acts as a strong solid acid catalyst.

Example 4

Figure 4:
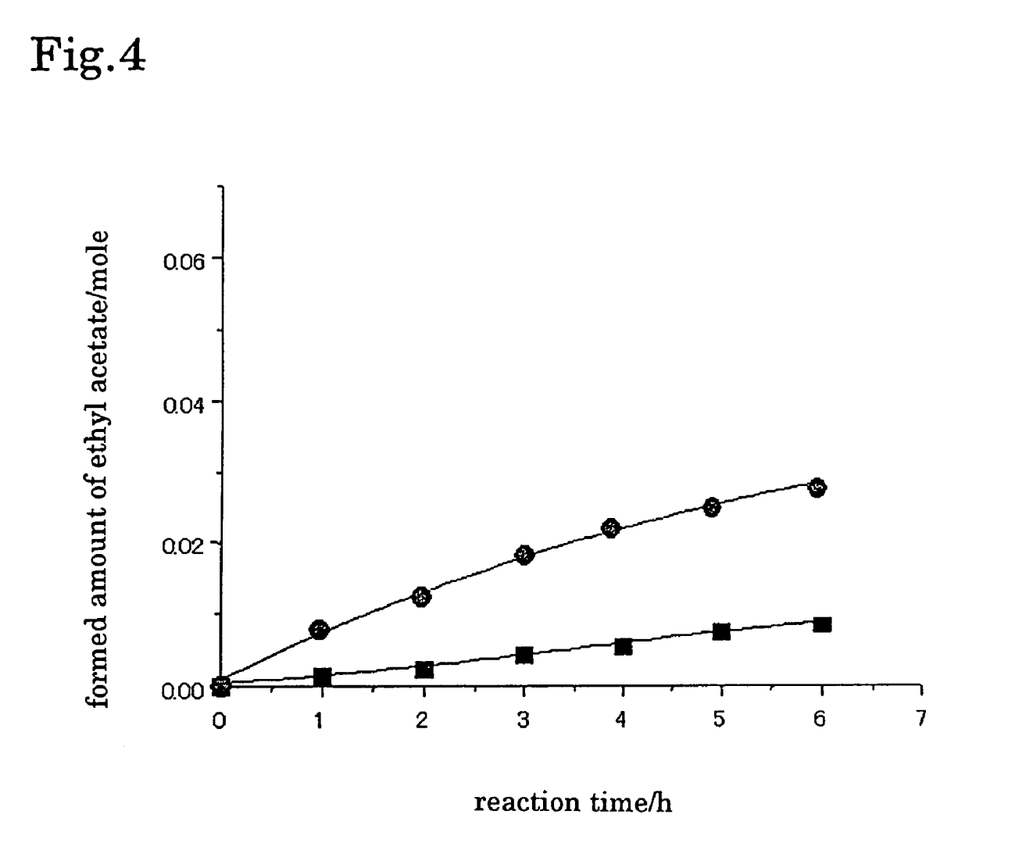
FIG. 4 shows catalytic activity of a solid acid obtained in Example 4 when it is used as an acid catalyst for esterfication reaction of ethanol and acetic acid.

1.00 g of coronene ($C_{24}H_{12}$) is poured into a flask with a reflux condenser in which 20 mL of fuming sulfuric acid ($SO_3$:25%) is contained and refluxed at 150° C. for 2 hours. Excess conc. sulfuric acid is removed by vacuum distillation at 250° C., then black solid powder is obtained. This solid powder is washed by 300 mL of ethyl alcohol, and the washing process is repeated until sulfuric acid contained in ethyl alcohol after washed becomes under detection limit of elementary analysis. Since from X-ray diffraction pattern of the obtained black powder, any structure is not observed, this material is understood to be amorphous. From elementary analysis using CHNS-932, which is a product of LECO Co., Ltd., USA, sulfur content of this polycyclic aromatic carbon solid strong acid is 0.5 atm %, and presence of many sulfonic acid groups are detected. From the results of temperature-programmed desorption and thermogravimetric analysis, it is confirmed that the decomposition temperature of the polycyclic aromatic carbon solid strong acid in atmosphere is 210° C., and is understood that thermo stability of it is high. Above mentioned black powder is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 4. In FIG. 4, for the comparison, formation of ethyl acetate by reaction without catalyst is also shown by time lapse. As shown in FIG. 4, forming speed of ethyl acetate in the presence of synthesized catalyst is remarkably high, and it is understood that the synthesized material acts as a strong solid acid catalyst.

Example 5

Figure 5:
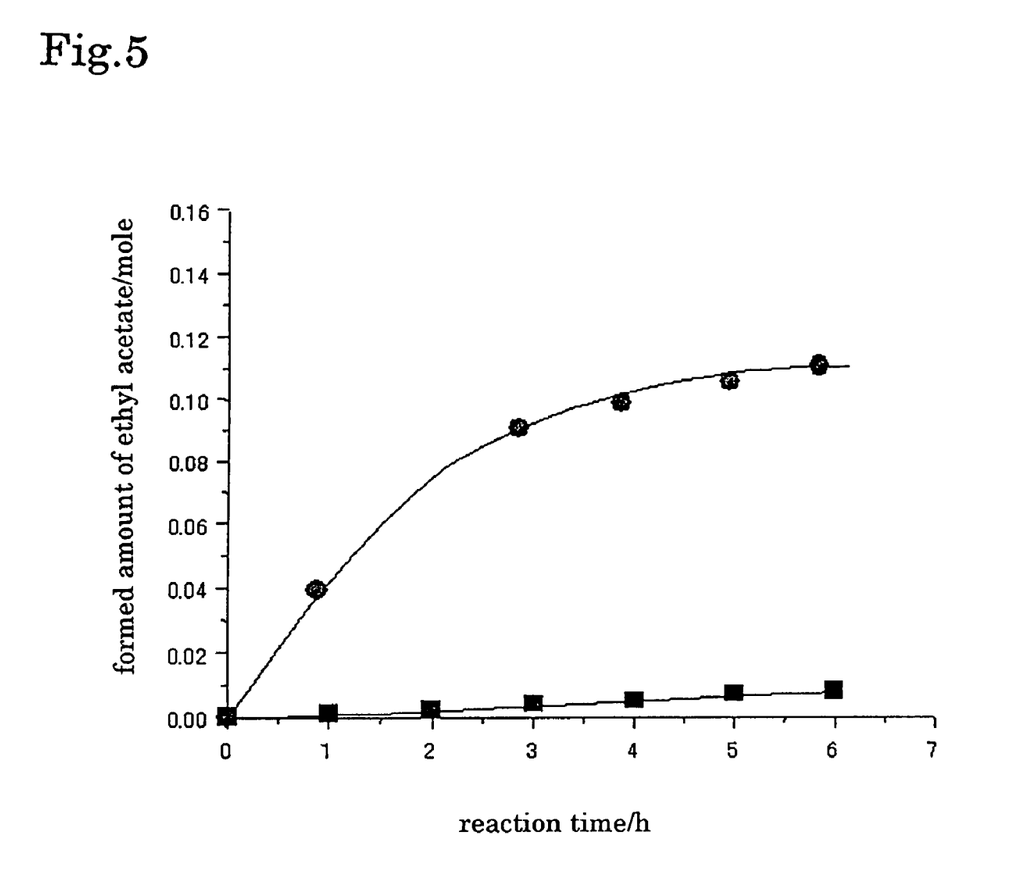
FIG. 5 shows catalytic activity of a solid acid obtained in Example 5 when it is used as an acid catalyst for esterfication reaction of ethanol and acetic acid.

2.00 g of petroleum pitch is added to 100 mL of conc. sulfuric acid (96%) and heated at 300° C. for 8 hours. Excess conc. sulfuric acid is removed by vacuum distillation at 300° C., then black solid powder is obtained. This solid powder is washed by 300 mL of ethyl alcohol, and the washing process is repeated until sulfuric acid contained in ethyl alcohol after washed becomes under detection limit of elementary analysis. Since from X-ray diffraction pattern of the obtained black powder, any structure is not observed, this material is understood to be amorphous. From elementary analysis, sulfur content of this polycyclic aromatic carbon solid strong acid is 3.5 atm %, and presence of many sulfonic acid groups are detected. From the results of temperature-programmed desorption and thermogravimetric analysis, it is confirmed that the decomposition temperature of the polycyclic aromatic carbon solid strong acid in atmosphere is 210° C., and is understood that thermo stability of it is high. Above mentioned black powder is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 5. In FIG. 5, for the comparison, formation of ethyl acetate by reaction without catalyst is also shown by time lapse. As shown in FIG. 5, forming speed of ethyl acetate in the presence of synthesized catalyst is remarkably high, and it is understood that the synthesized material using petroleum pitch as a starting material acts as a strong solid acid catalyst.

Example 6

20 g of naphthalene is added to 300 mL of conc. sulfuric acid (96%) and heated at 250° C. for 15 hours. Excess conc. sulfuric acid is removed by vacuum distillation at 250° C., then black solid powder of polycyclic aromatic carbon solid strong acid is obtained. This polycyclic aromatic carbon solid strong acid is washed by 300 mL of distilled water at 90° C., and the washing process is repeated until sulfuric acid contained in water after washed becomes under detection limit of elementary analysis. From X-ray diffraction pattern of the obtained insulating polycyclic aromatic carbon solid strong acid any structure is not observed, therefore, this material is understood to be an amorphous material. From elementary analysis, sulfur content of this polycyclic aromatic carbon solid strong acid is 7.1 atm %, and presence of many sulfonic acid groups are detected. From the results of temperature-programmed desorption and thermogravimetric analysis, it is confirmed that the decomposition temperature of the polycyclic aromatic carbon solid strong acid in atmosphere is 250° C., and is understood that thermo stability of it is high.

Figure 6:
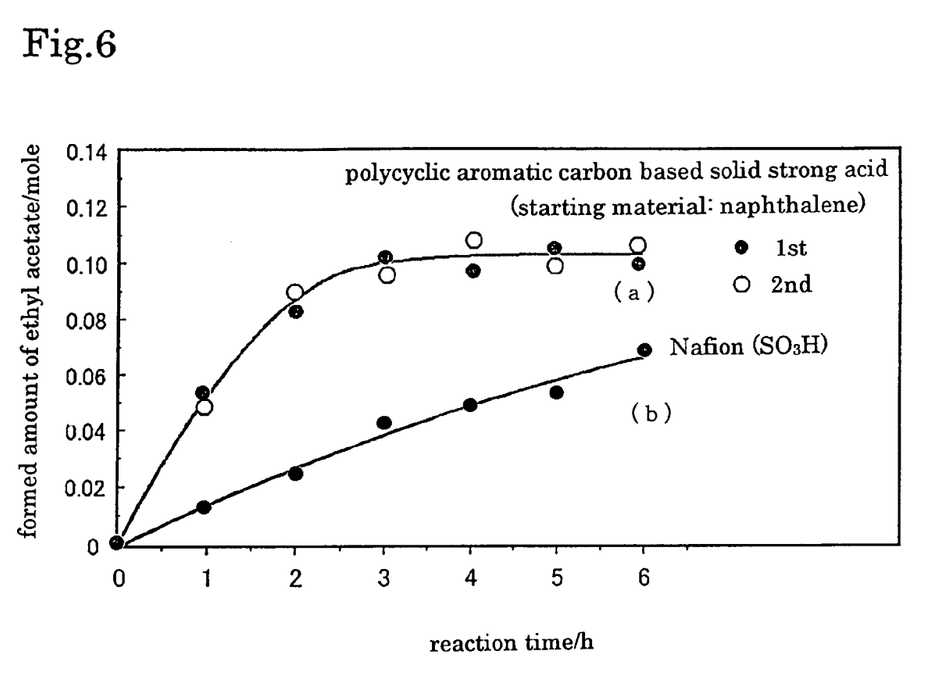
FIG. 6 shows catalytic activity of a solid acid obtained in Example 6 when it is used as an acid catalyst for esterfication reaction of ethanol and acetic acid (●shows activity of first time use and ○ shows activity of $2^{nd}$ time use. These marks are same in FIGS. 7-10).

Above mentioned polycyclic aromatic carbon solid strong acid is evacuated at 150° C. for 1 hour, then 0.2 g of it is added as a catalyst into mixed solution of 0.1 mol acetic acid and 10 mol ethyl alcohol under argon gas flow, stirred at 70° C. for 6 hours and the amount of ethyl acetate formed by acid catalyst reaction is detected by a gas chromatography. Results are shown in FIG. 6(*a*). In FIG. 6, for the comparison, formation of ethyl acetate by reaction using same amount of $SO_3H$ Nafion as a catalyst is also shown by time lapse (b). As shown in the Figure, in the presence of the synthesized catalyst, formation speed of ethyl acetate is very fast and it is understood that the synthesized material is a solid acid catalyst having stronger acid strength than that of Nafion (●). After reaction, recovered material is washed, then used as a catalyst of same reaction. Results are shown in FIG. 6 (○). As clearly understood from FIG. 6, acid catalytic activity of polycyclic aromatic carbon solid strong acid does not deteriorate by repeating use. Further, said synthesized polycyclic aromatic carbon solid strong acid is heated with distilled water in an autoclave of 150° C. for 72 hours and filtrated. This filtrated powder is evacuated for 1 hour at 150° C., then 0.2 g of it is used as a catalyst and same reaction as mentioned above is carried out. Catalytic activity of it is same as to the case of FIG. 6. These results indicate that said polycyclic aromatic carbon solid strong acid is chemically stable and acid strength of it is not deteriorated even in hot water of 150° C.

Example 7

10 g of fuel oil (A fuel oil) is added to 300 mL of conc. sulfuric acid (96%) and heated at 250° C. for 15 hours. Excess conc. sulfuric acid is removed by vacuum distillation at 250° C., and then black solid powder of polycyclic aromatic carbon solid strong acid is obtained. This polycyclic aromatic carbon solid strong acid is washed by 300 mL of distilled water at 90° C., and the washing process is repeated until sulfuric acid contained in water after washed becomes under detection limit of elementary analysis. From X-ray diffraction pattern of the obtained insulating polycyclic aromatic carbon solid strong acid any structure is not observed, therefore, this material is understood to be an amorphous material. From elementary analysis, sulfur content of this polycyclic aromatic carbon solid strong acid is 8.5 atm %, and presence of many sulfonic acid groups are detected. From the results of temperature-programmed desorption and thermogravimetric analysis, it is confirmed that the decomposition temperature of the polycyclic aromatic carbon solid strong acid in atmosphere is 230° C., and is understood that thermo stability of it is high.

Figure 7:
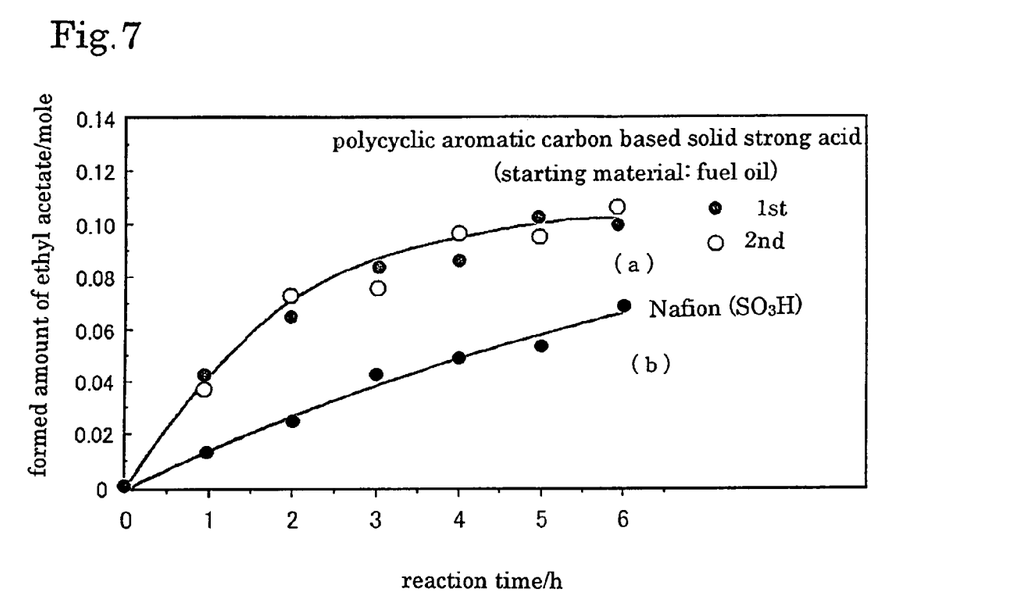
FIG. 7 shows catalytic activity of a solid acid obtained in Example 7 when it is used as an acid catalyst for esterfication reaction of ethanol and acetic acid.

Above mentioned polycyclic aromatic carbon solid strong acid is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 7(a). In FIG. 7, for the comparison, formation of ethyl acetate by reaction using same amount of SO$_3$H Nafion as a catalyst is also shown by time lapse (b). As shown in the Figure, in the presence of the synthesized catalyst, formation speed of ethyl acetate is very fast and it is understood that the synthesized material is a solid acid catalyst having stronger acid strength than that of Nafion (●). After reaction, recovered material is washed, then used as a catalyst of same reaction. Results are shown in FIG. 7 (○). As clearly understood from FIG. 7, acid catalytic activity of polycyclic aromatic carbon solid strong acid does not deteriorate by repeating use. Further, said synthesized polycyclic aromatic carbon solid strong acid is heated with distilled water in an autoclave of 150° C. for 72 hours and filtered. This filtered powder is evacuated for 1 hour at 150° C., then 0.2 g of it is used as a catalyst and same reaction as mentioned above is carried out. Catalytic activity of it is same as to the case of FIG. 7. These results indicate that said polycyclic aromatic carbon solid strong acid is chemically stable and acid strength of it is not deteriorated even in hot water of 150° C.

Example 8

5 g of asphalt is added to 300 mL of conc. sulfuric acid (96%) and heated at 250° C. for 15 hours. Excess conc. sulfuric acid is removed by vacuum distillation at 250° C., and then black solid powder of polycyclic aromatic carbon solid strong acid is obtained. This polycyclic aromatic carbon solid strong acid is washed by 300 mL of distilled water at 90° C., and the washing process is repeated until sulfuric acid contained in water after washed becomes under detection limit of elementary analysis. From X-ray diffraction pattern of the obtained insulating polycyclic aromatic carbon solid strong acid any structure is not observed, therefore, this material is understood to be an amorphous material. From elementary analysis, sulfur content of this polycyclic aromatic carbon solid strong acid is 5.5 atm %, and presence of many sulfonic acid groups are detected. From the results of temperature-programmed desorption and thermogravimetric analysis, it is confirmed that the decomposition temperature of the polycyclic aromatic carbon solid strong acid in atmosphere is 280° C., and is understood that thermo stability of it is high.

Figure 8:
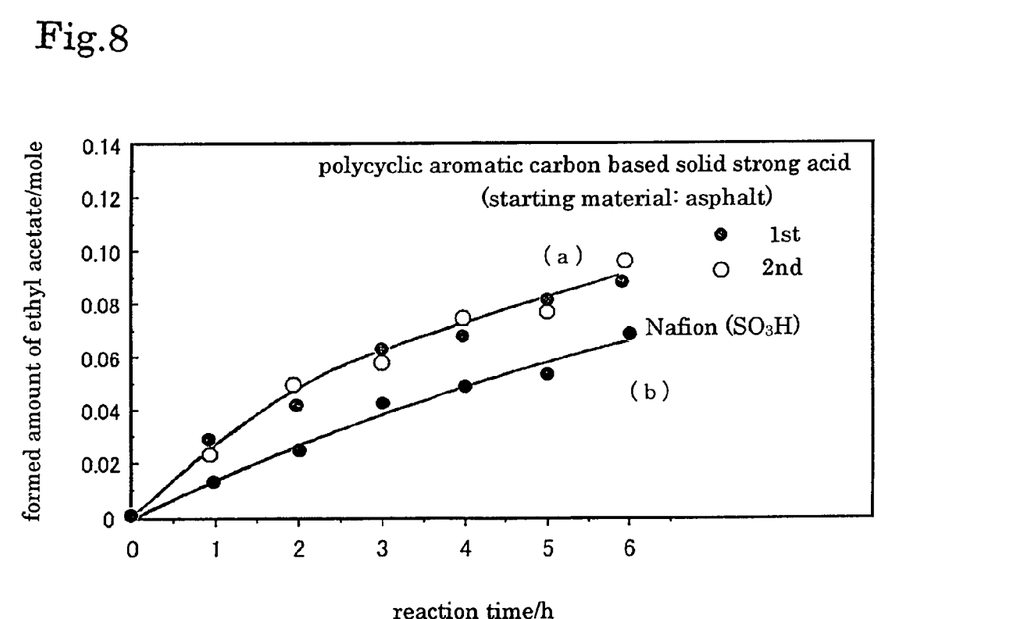
FIG. 8 shows catalytic activity of a solid acid obtained in Example 8 when it is used as an acid catalyst for esterfication reaction of ethanol and acetic acid.

Above mentioned polycyclic aromatic carbon solid strong acid is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 8(a). In FIG. 8, for the comparison, formation of ethyl acetate by reaction using same amount of SO$_3$H Nafion as a catalyst is also shown by time lapse (b). As shown in the Figure, in the presence of the synthesized catalyst, formation speed of ethyl acetate is very fast and it is understood that the synthesized material is a solid acid catalyst having stronger acid strength than that of Nafion (●). After reaction, recovered material is washed, then used as a catalyst of same reaction. Results are shown in FIG. 8 (○). As clearly understood from FIG. 8, acid catalytic activity of polycyclic aromatic carbon solid strong acid does not deteriorate by repeating use. Further, said synthesized polycyclic aromatic carbon solid strong acid is heated with distilled water in an autoclave of 150° C. for 72 hours and filtrated. This filtrated powder is evacuated for 1 hour at 150° C., then 0.2 g of it is used as a catalyst and same reaction as mentioned above is carried out. Catalytic activity of it is same as to the case of FIG. 8. These results indicate that said polycyclic aromatic carbon solid strong acid is chemically stable and acid strength of it is not deteriorated even in hot water of 150° C.

Example 9

Polycyclic aromatic carbon solid strong acid—carbon material composite 5 g of naphthalene and 5 g of activated carbon are added to 300 mL of conc. sulfuric acid (96%) and heated at 250° C. for 15 hours. Excess conc. sulfuric acid is removed by vacuum distillation at 250° C., and then black solid powder of polycyclic aromatic carbon solid strong acid—carbon material composite is obtained. This aromatic carbon solid strong acid—carbon material composite is washed by 300 mL of distilled water at 90° C., and the washing process is repeated until sulfuric acid contained in water after washed becomes under detection limit of elementary analysis. From elementary analysis, sulfur content of this polycyclic aromatic carbon solid strong acid is 3.5 atm %, and presence of many sulfonic acid groups are detected. From the results of temperature-programmed desorption and thermogravimetric analysis, it is confirmed that the decomposition temperature of the polycyclic aromatic carbon solid strong acid—carbon material composite in atmosphere is 230° C., and is understood that thermo stability of it is high.

Figure 9:
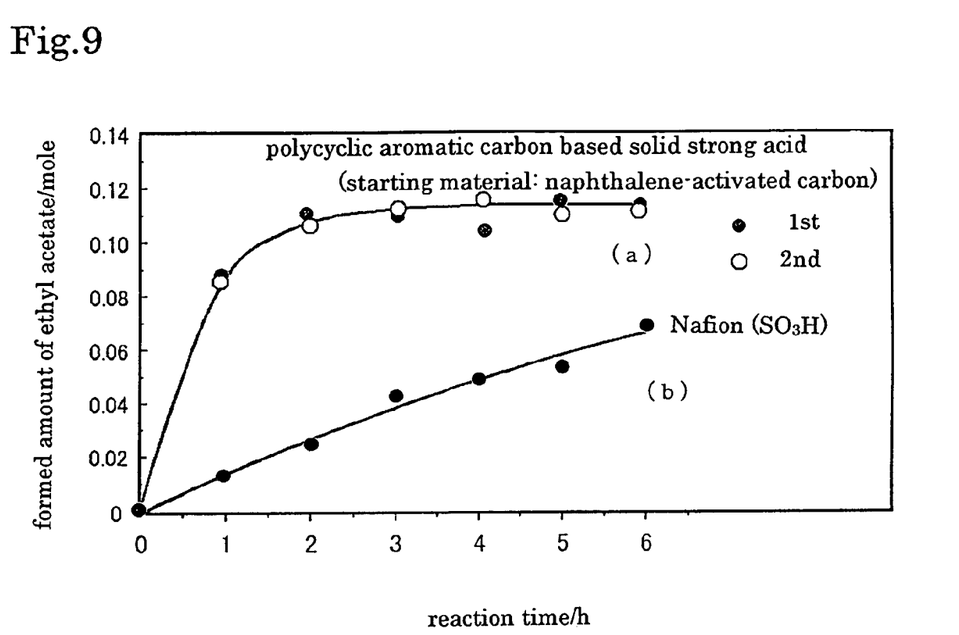
FIG. 9 shows catalytic activity of a solid acid obtained in Example 9 when it is used as an acid catalyst for esterfication reaction of ethanol and acetic acid.

Above mentioned polycyclic aromatic carbon solid strong acid—carbon material composite is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 9(a). In FIG. 9, for the comparison, formation of ethyl acetate by reaction using same amount of SO$_3$H Nafion as a catalyst is also shown by time lapse (b). As shown in the Figure, in the presence of the synthesized catalyst, formation speed of ethyl acetate is very fast and it is understood that the synthesized material is a solid acid catalyst having stronger acid strength than that of Nafion (●). Further, it is confirmed that the obtained polycyclic aromatic carbon solid strong acid—carbon material composite indicates stronger activity than that of polycyclic aromatic carbon solid strong acid whose starting material is naphthalene alone, and it is also confirmed that acid catalytic activity can be improved by adhering polycyclic aromatic carbon solid strong acid to the surface of activated carbon having broad surface area. After reaction, recovered material is washed, then used as a catalyst of same reaction. Results are shown in FIG. 9 (○). As clearly understood from FIG. 9, acid catalytic activity of polycyclic aromatic carbon solid strong acid—carbon material composite does not deteriorate by repeating use. Further, said synthesized polycyclic aromatic carbon solid strong acid—carbon material composite is heated with distilled water in an autoclave of 150° C. for 72 hours and filtrated. This filtrated powder is evacuated for 1 hour at 150° C., then 0.2 g of it is used as a catalyst and same reaction as mentioned above is carried out. Catalytic activity of it is same as to the case of FIG. 9.

These results indicate that said polycyclic aromatic carbon solid strong acid —carbon material composite is chemically stable and acid strength of it is not deteriorated even in hot water of 150° C.

Example 10

5 g of naphthalene and 5 g of acetylene black are added to 300 mL of conc. sulfuric acid (96%) and heated at 250° C. for 15 hours. Excess conc. sulfuric acid is removed by vacuum distillation at 250° C., and then black solid powder of polycyclic aromatic carbon solid strong acid—carbon material composite is obtained. This aromatic carbon solid strong acid—carbon material composite is washed by 300 mL of distilled water at 90° C., and the washing process is repeated until sulfuric acid contained in water after washed becomes under detection limit of elementary analysis. From elementary analysis, sulfur content of this polycyclic aromatic carbon solid strong acid is 4.7 atm %, and presence of many sulfonic acid groups are detected. From the results of temperature-programmed desorption and thermogravimetric analysis, it is confirmed that the decomposition temperature of the polycyclic aromatic carbon solid strong acid—carbon material composite in atmosphere is 230° C., and is understood that thermo stability of it is high.

Figure 10:
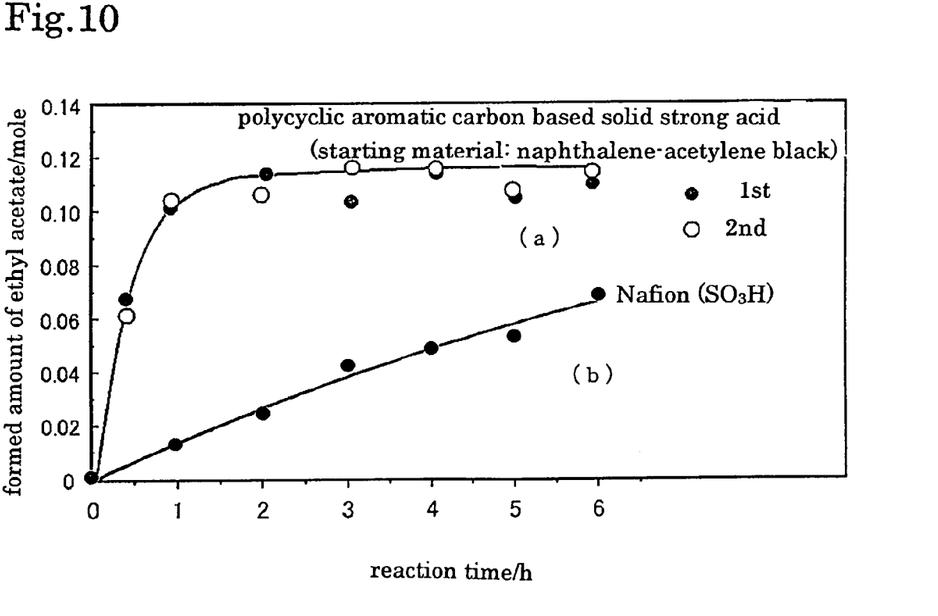
FIG. 10 shows catalytic activity of a solid acid obtained in Example 10 when it is used as an acid catalyst for esterfication reaction of ethanol and acetic acid.

Above mentioned polycyclic aromatic carbon solid strong acid—carbon material composite is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 10(a). In FIG. 10, for the comparison, formation of ethyl acetate by reaction using same amount of $SO_3H$ Nafion as a catalyst is also shown by time lapse (b). As shown in the Figure, in the presence of the synthesized catalyst, formation speed of ethyl acetate is very fast and it is understood that the synthesized material is a solid acid catalyst having stronger acid strength than that of Nafion (●). Further, it is confirmed that the obtained polycyclic aromatic carbon solid strong acid—carbon material composite indicates stronger activity than that of polycyclic aromatic carbon solid strong acid whose starting material is naphthalene alone, and it is also confirmed that acid catalytic activity can be improved by adhering polycyclic aromatic carbon solid strong acid to the surface of acetylene black having broad surface area.

After reaction, recovered material is washed, and then used as a catalyst of same reaction. Results are shown in FIG. 10 (○). As clearly understood from FIG. 10, acid catalytic activity of polycyclic aromatic carbon solid strong acid—carbon material composite does not deteriorate by repeating use. Further, said synthesized polycyclic aromatic carbon solid strong acid—carbon material composite is heated with distilled water in an autoclave of 150° C. for 72 hours and filtrated. This filtrated powder is evacuated for 1 hour at 150° C., then 0.2 g of it is used as a catalyst and same reaction as mentioned above is carried out. Catalytic activity of it is same as to the case of FIG. 10. These results indicate that said polycyclic aromatic carbon solid strong acid—carbon material composite is chemically stable and acid strength of it is not deteriorated even in hot water of 150° C.

Comparative Example 1

1.00 g of coronene ($C_{24}H_{12}$) is added to 100 mL of conc. sulfuric acid (96%) and heated at 50° C. for 8 hours, then centrifuged by 3000 rpm rotating speed for 30 minutes, however solid is not separated. It is considered that by the temperature condition of 50° C., polycondensation of aromatic rings is not sufficient and sulfonated polycyclic aromatic carbon solid strong acid can not be existed as an insoluble solid.

Comparative Example 2

1.00 g of coronene ($C_{24}H_{12}$) is added to 100 mL of conc. sulfuric acid (96%) and heated at 500° C. for 2 hours, and black solid powder is obtained. This solid powder is washed by 300 mL of ethyl alcohol, and the washing process is repeated until sulfuric acid contained in ethyl alcohol after washed becomes under detection limit of elementary analysis. Since from X-ray diffraction pattern of the obtained black powder, any structure is not observed, this material is understood to be amorphous. From elementary analysis, sulfur content of this polycyclic aromatic carbon solid strong acid is 0.05 atm %. Above mentioned black powder is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. The forming speed of ethyl acetate is not so much different from the state of without catalyst and is clearly understood that the synthesized material does not act as a solid acid catalyst. For the quantitative analysis of sulfur amount loaded to the surface, X-ray photoelectron spectroscopic spectrum of said black powder is measured, and from the result it become clear that sulfur is not exist on the surface. The reason why is considered as follows, that is, when temperature for treatment is too high, sulfone groups on surface are decomposed.

Comparative Example 3

Figure 11:
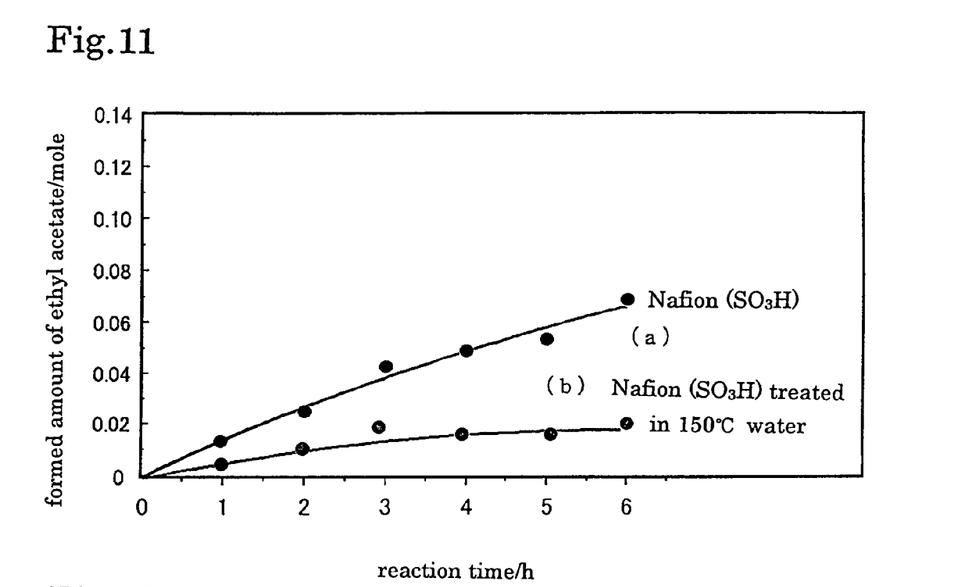
FIG. 11 shows catalytic activity of an acid catalyst composed of $SO_3H$ type Nafion powder (product of Du pont) of Comparative Example 3 when it is used as an acid catalyst for esterfication reaction of ethanol and acetic acid.

Proton exchanged $SO_3H$ Nafion powder (product of Du'pont) is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 11(a). Formation of ethyl acetate is progressed under the presence of Nafion. After reaction, recovered material is washed, and then used as a catalyst of same reaction. Results are shown in FIG. 11. As clearly understood from FIG. 11, acid catalytic activity of Nafion does not deteriorate by repeating use. Further, said synthesized polycyclic aromatic carbon solid strong acid is heated with distilled water in an autoclave of 150° C. for 72 hours and filtrated. This filtrated powder is evacuated for 1 hour at 150° C., then 0.2 g of it is used as a catalyst and same reaction as mentioned above is carried out. As shown in FIG. 11, catalytic activity of it is remarkably deteriorated (b). These results indicates that the stability of Nafion is lower than that of said polycyclic aromatic carbon solid strong acid—carbon material composite and acid strength of Nafion deteriorate in water of 150° C.

Comparative Example 4

Figure 12:
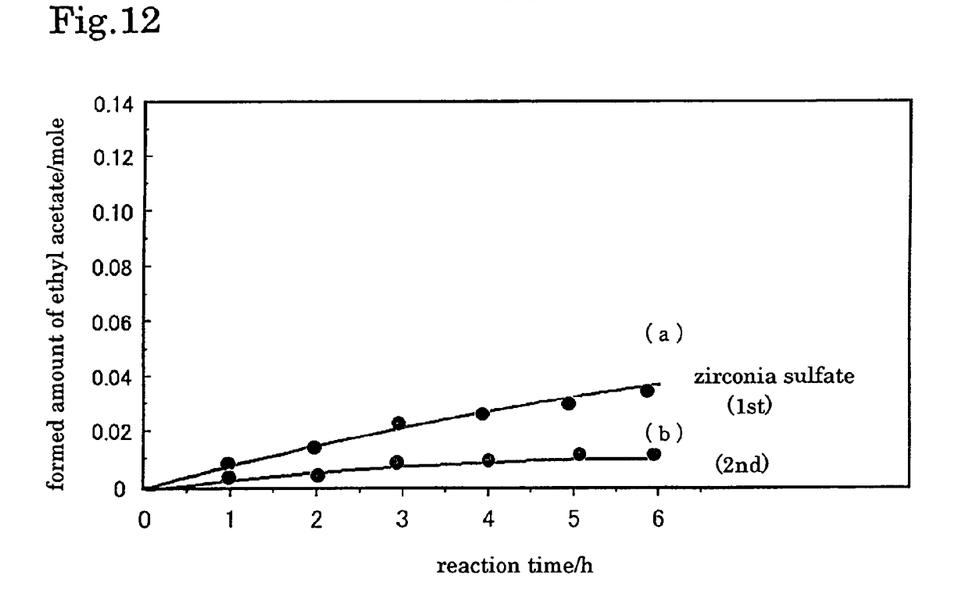
FIG. 12 shows catalytic activity of an acid catalyst composed of zirconia sulfate (product of Wako Junyaku) of Comparative Example 4 at first time use and $2^{nd}$ time use.

Zirconia sulfate (product of Wako Junyaku Co., Ltd.) is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 12. Formation of ethyl acetate is progressed under the presence of zirconia sulfate (●). After reaction, recovered material is washed, and then used as a catalyst of same reaction. Results are shown in FIG. 12 (○). As clearly understood by the Figure, acid catalytic activity of zirconia sulfate remarkably deteriorated by repeating use, and sulfuric acid trace on the surface of zirconia sulfate is unstable in water.

Comparative Example 5

5 g of activated carbon is added to 300 mL of conc. sulfuric acid (96%) and heated at 250° C. for 15 hours. Excess conc. sulfuric acid is removed by vacuum distillation at 250° C., and then black powder is obtained. This black powder is washed by 300 mL of distilled water at 90° C., and the washing process is repeated until sulfuric acid contained in water after washed becomes under detection limit of elementary analysis. From elementary analysis, sulfur content of this polycyclic aromatic carbon solid strong acid—carbon material composite is confirmed to be smaller than 0.05 atm %. X-ray diffraction pattern of the obtained black powder is same as X-ray diffraction pattern of the activated carbon before heat treatment in conc. sulfuric acid.

Figure 13:
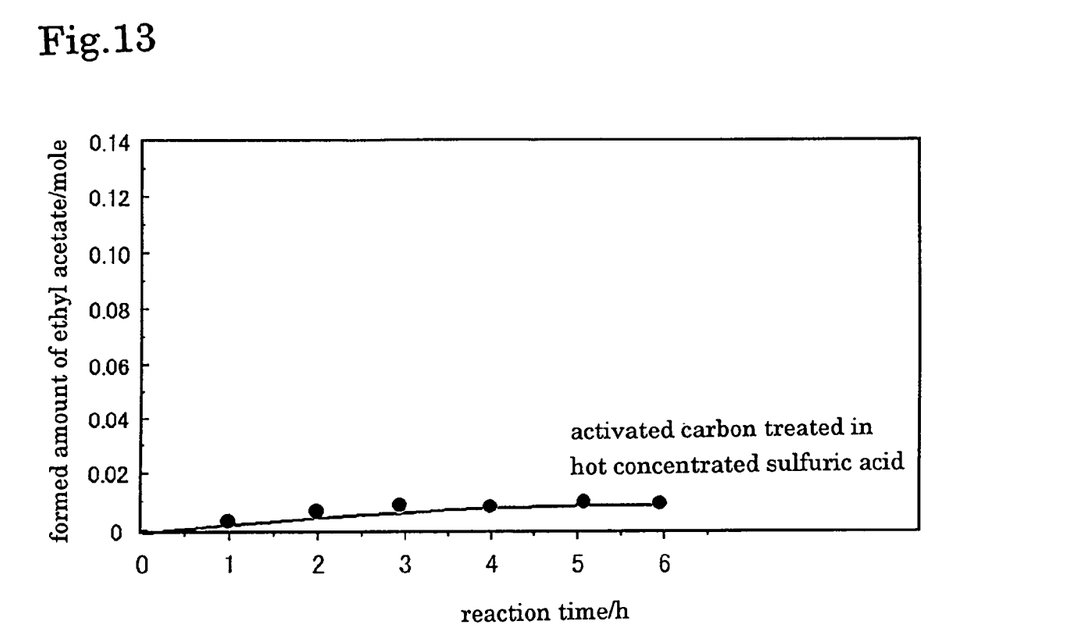
FIG. 13 shows catalytic activity of an activated carbon treated by concentrated sulfuric acid (96%) of Comparative Example 5 when it is used as an acid catalyst for esterification reaction of ethanol and acetic acid.

Above mentioned black powder is evacuated at 150° C. for 1 hour, then 0.2 g of it is added as a catalyst into mixed solution of 0.1 mol acetic acid and 1.0 mol ethyl alcohol under argon gas flow, stirred at 70° C. for 6 hours and the amount of ethyl acetate formed by acid catalyst reaction is detected by a gas chromatography. Results are shown in FIG. 13. Cleary understood from the Figure, forming speed of ethyl acetate is slow under the presence of synthesized catalyst, and is confirmed that acid catalytic function of the synthesized material is very small.

INDUSTRIAL APPLICABILITY

Solid strong acid or solid strong acid—carbon material composite of the present invention which are insoluble in a polar solvent is a material having strong acid characteristic produced by relatively easy method using cheap material, therefore, brings an excellent effect that are advantageous from view points of cost, function and industry.

What is claimed is:

1. A solid acid, which is insoluble in a polar solvent, obtained by heat treating of polycyclic aromatic hydrocarbons in concentrated sulfuric acid or fuming sulfuric acid to thereby condense and sulfonate said polycyclic aromatic hydrocarbons wherein temperature T for heat treatment is 200° C.$\leq$T$\leq$450° C.

2. The solid acid of claim 1, wherein polycyclic aromatic hydrocarbons is at least one selected from the group consisting of a polycyclic aromatic hydrocarbon obtained by condensing two or more aromatic rings, mixture of a polycyclic aromatic hydrocarbon obtained by condensing two or more aromatic rings or tar, pitch, fuel oil or asphalt containing a polycyclic aromatic hydrocarbon obtained by condensing two or more aromatic rings.

3. The solid acid of claim 2, wherein temperature T for heat treatment is 200° C.$\leq$T$\leq$350° C.

4. A solid strong acid catalyst comprising, a solid acid, which is insoluble in a polar solvent, obtained by heat treating of polycyclic aromatic hydrocarbons in concentrated sulfuric acid or fuming sulfuric acid to thereby to concentrate and sulfonate said polycyclic aromatic hydrocarbons wherein temperature T for heat treatment is 200° C.$\leq$T$\leq$450° C.

5. The solid strong acid catalyst of claim 4, wherein polycyclic aromatic hydrocarbons is at least one selected from the group consisting of a polycyclic aromatic hydrocarbon obtained by condensing two or more aromatic rings, mixture of a polycyclic aromatic hydrocarbon obtained by condensing two or more aromatic rings or tar, pitch, fuel oil or asphalt containing a polycyclic aromatic hydrocarbon obtained by condensing two or more aromatic rings.

6. The solid strong acid catalyst of claim 5, wherein temperature T for heat treatment is 200° C.$\leq$T$\leq$350° C.

7. A composite solid strong acid comprising, a solid acid and a carbon material, wherein said solid acid is obtained by heat treating of polycyclic aromatic hydrocarbons to which the carbon material is blended in concentrated sulfuric acid or fuming sulfuric acid, transforming said polycyclic aromatic hydrocarbons to a solid acid which is insoluble in a polar solvent by condensation and sulfonation further compositing with said carbon material wherein temperature T for heat treatment is 200° C.$\leq$T$\leq$450° C.

8. The composite solid strong acid of claim 7, wherein polycyclic aromatic hydrocarbons is at least one selected from the group consisting of a polycyclic aromatic hydrocarbon obtained by condensing two or more aromatic rings, mixture of a polycyclic aromatic hydrocarbon obtained by condensing two or more aromatic rings or tar, pitch, fuel oil or asphalt containing a polycyclic aromatic hydrocarbon obtained by condensing two or more aromatic rings.

9. The composite solid strong acid of claim 8, wherein temperature T for heat treatment is 200° C.$\leq$T$\leq$350° C.

10. The composite solid strong acid according to claim 7, wherein the carbon material is at least one selected from the group consisting of carbon black, acetylene black, activated carbon, carbon nano tube or fullerene.

11. The solid acid of claim 10, wherein temperature T for heat treatment is 200° C.$\leq$T$\leq$350° C.

12. The composite solid strong acid according to claim 8, wherein the carbon material is at least one selected from the group consisting of carbon black, acetylene black, activated carbon, carbon nano tube or fullerene.

13. The composite solid strong acid according to claim 9, wherein the carbon material is at least one selected from the group consisting of carbon black, acetylene black, activated carbon, carbon nano tube or fullerene.

14. A composite solid strong acid comprising, a solid acid and a carbon material, wherein said solid acid is obtained by heat treating of polycyclic aromatic hydrocarbons to which the carbon material is blended in concentrated sulfuric acid or fuming sulfuric acid, transforming said polycyclic aromatic hydrocarbons to a solid acid which is insoluble in a polar solvent by condensation and sulfonation further compositing with said carbon material, wherein the carbon material is at least one selected from the group consisting of carbon black, acetylene black, activated carbon, carbon nano tube or fullerene.

15. The composite solid strong acid of claim 14, wherein polycyclic aromatic hydrocarbons is at least one selected from the group consisting of a polycyclic aromatic hydrocarbon obtained by condensing two or more aromatic rings, mixture of a polycyclic aromatic hydrocarbon obtained by condensing two or more aromatic rings or tar, pitch, fuel oil or asphalt containing a polycyclic aromatic hydrocarbon obtained by condensing two or more aromatic rings, wherein the carbon material is at least one selected from the group consisting of carbon black, acetylene black, activated carbon, carbon nano tube or fullerene.

16. The composite solid strong acid of claim 14, wherein temperature T for heat treatment is $100° C. \leq T \leq 450° C.$, wherein the carbon material is at least one selected from the group consisting of carbon black, acetylene black, activated carbon, carbon nano tube or fullerene.

17. The composite solid strong acid of claim 14, wherein temperature T for heat treatment is $200° C. \leq T \leq 350° C.$, wherein the carbon material is at least one selected from the group consisting of carbon black, acetylene black, activated carbon, carbon nano tube or fullerene.

* * * * *